(12) United States Patent
Pridmore et al.

(10) Patent No.: US 7,875,421 B2
(45) Date of Patent: Jan. 25, 2011

(54) **LA1—THE GENOME OF A *LACTOBACILLUS* STRAIN**

(75) Inventors: Raymond David Pridmore, Lausanne (CH); Beat Mollet, Lausanne (CH); Fabrizio Arigoni, Genève (CH); Josef Hermanns, Epfenbach (DE)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 12/244,581

(22) Filed: Oct. 2, 2008

(65) Prior Publication Data

US 2009/0098053 A1    Apr. 16, 2009

Related U.S. Application Data

(60) Division of application No. 10/961,644, filed on Oct. 8, 2004, now abandoned, which is a continuation of application No. PCT/EP03/02882, filed on Mar. 19, 2003.

(30) Foreign Application Priority Data

Apr. 9, 2002    (EP)    ................... 02007932

(51) Int. Cl.
  *C12Q 1/00*    (2006.01)
  *G01N 33/554*    (2006.01)
(52) U.S. Cl. .......................................... 435/4; 435/7.32
(58) Field of Classification Search ....................... None
  See application file for complete search history.

(56) References Cited

U.S. PATENT DOCUMENTS

| 5,603,930 | A | * | 2/1997 | Brassart et al. | .......... 424/93.45 |
| 5,652,838 | A | | 7/1997 | Lovett et al. | |
| 5,815,333 | A | | 9/1998 | Yamamoto et al. | |
| 6,005,728 | A | | 12/1999 | Bang | |
| 6,110,725 | A | | 8/2000 | Delley et al. | |
| 6,258,587 | B1 | | 7/2001 | Delley et al. | |
| 6,410,016 | B2 | * | 6/2002 | Maruta et al. | ............ 424/93.45 |
| 6,929,793 | B2 | * | 8/2005 | Spivey-Krobath et al. | .. 424/93.4 |
| 2003/0049231 | A1 | * | 3/2003 | Baur et al. | ................. 424/93.4 |

FOREIGN PATENT DOCUMENTS

| EP | 0 768 375 | 4/1997 |
| EP | 0 875 579 | 4/1998 |
| WO | 96 33276 | 10/1996 |
| WO | WO 02/12506 A1 * | 2/2002 |

OTHER PUBLICATIONS ("elucidate." Merriam-Webster Online Dictionary. 2009. Merriam-Webster Online. Dec. 14, 2009 http://www.merriam-webster.com/dictionary/elucidate).*
Pfeifer et al., "Probiotics in Alimentation: Clinical Evidence for Their Enhancement of the Natural Immunity of the Gut," Probiotics, Other Nutritional Factors, and Intestinal Microflora, Nestle Nutrition Workshop Series, vol. 42, pp. 243-257, XP-001104004.
Walker D.C., et al., IS Elements are Associated with the Lactacin F Operon of *Lactobacillus johnsonii* NCC533, One of Which Disrupts a Two-Component Signaling System and Bacteriocin Production, Abstracts of the General Meeting of the American Society, 100th General Meeting of the American Society for Microbiology; Los Angeles, vol. 100, 2000, p. 361, XP008007077.
Kim et al., "Conservation of the Major Cold Shock Protein in Lactic Acid Bacteria," Current Microbiology, vol. 37 (1998), pp. 333-336.

* cited by examiner

*Primary Examiner*—Mark Navarro
(74) *Attorney, Agent, or Firm*—K&L Gates LLP

(57) ABSTRACT

The present invention pertains to the use of the DNA sequence of a *Lactobacillus johnsonii* strain, in particular to its genomic sequence for elucidating interactions of microorganism with hosts they colonize, and moreover for elucidating the basis of probiotic properties exhibited by such strain. In addition, the present invention also relates to methods of detecting nucleic acids or polypeptides of *Lactobacilli* and related species, respectively. A data carrier is provided comprising nucleotide sequences and/or polypeptide sequences of La1.

4 Claims, No Drawings

LA1—THE GENOME OF A *LACTOBACILLUS* STRAIN

CROSS-REFERENCE TO RELATED APPLICATIONS

This application is a divisional of patent application Ser. No. 10/961,644, filed Oct. 8, 2004, now abandoned which is a continuation of International application PCT/EP03/02882 filed Mar. 19, 2003, the entire content of patent application Ser. No. 10/961,644 and PCT/EP03/02882 are expressly incorporated herein by reference.

BACKGROUND

The present invention pertains to the use of the DNA sequence of a *Lactobacillus johnsonii* strain, in particular to its genomic sequence for elucidating interactions of microorganism with hosts they colonize, and moreover for elucidating the basis of probiotic properties exhibited by such strain. In addition, the present invention also relates to methods of detecting nucleic acids or polypeptides of *Lactobacilli* and related species, respectively. A data carrier is provided comprising nucleotide sequences and/or polypeptide sequences of La1.

Lactic acid bacteria, i.e. micro-organisms that produce lactic acid during their (fermentative) activity, are known for a long time and comprise e.g. the genera *Lactococcus, Lactobacillus, Streptococcus, Bifidobacterium* and *Pediococcus*. These bacteria are usually prominent in milk and also in milk processing factories, respectively, living or decaying plants and represent a constituent of the intestinal micro-flora in mankind and animals.

Lactic acid bacteria have been utilized as agents for the preservation of food taking benefit of a lowering of the pH and the action of products generated during the fermentative activity thereof to e.g. inhibit the growth of spoilage bacteria. In addition, lactic acid bacteria have also been used for preparing a variety of different foodstuff such as cheese, yoghurt and other fermented dairy products from milk.

Lately, lactic acid bacteria have attracted a great deal of attention in that some strains have been found to exhibit valuable properties to man and animals upon ingestion. In particular, specific strains of the genus *Lactobacillus* and *Bifidobacterium* have been found to pass the gastro-intestinal tract in a viable and live form without getting destroyed in the upper part thereof, especially by the impact of the low pH prevailing in the stomach. Moreover, they were found to be able to colonize the intestinal mucosa, with their temporary or sustained presence in the gut being postulated to bring about numerous positive effects on the health of the living beings. These strains are generically termed probiotics.

EP 0 768 375 discloses such a specific strain of the genus *Bifidobacterium*, that is capable to become implanted in the intestinal flora. This *Bifidobacterium* strain is reported to assist in immuno-modulation, being capable to competitively exclude adhesion of pathogenic bacteria to intestinal cells, thus supporting the maintenance of the individual's health.

Apart from *Bifidobacteria*, also some strains of *Lactobacilli* have been found to exert favorable properties to humans, such as preventing colonization of the gut by pathogenic bacteria or obstructing rotaviral infection. In particular, PCT/EP02/00958 discloses such a strain having both of said properties.

In the last few years the food industry has applied such strains in products, such as milk drinks or fermented acidified milk products. Clinical studies performed with these products and/or the bacterial strains confirmed the notion that these kind of bacteria account for health promoting traits in vivo and may even be utilized for contending diseases, such as ulcers. In particular, a strain of the genus *Lactobacillus johnsonii* has proven to be capable to combat *Helicobacter*, an acknowledged cause of ulcer in man.

In view of these valuable properties particular strains of lactic acid bacteria may provide, there is a strong desire in the art for elucidating the molecular basics of these health promoting properties. In particular it would be of great interest to determine the substance or substances responsible for these effect(s). To this end, tools are required to study these micro-organisms in more detail, so as to clarify the molecular principles underlying the probiotic properties, such as interaction with the hosts, the phenomena of passing (survive in) different environmental conditions in the gut as well as having the capability to adhere to the intestine's mucosa and eventually the involvement in the enhancement of the immune system and defense against pathogens, which information will allow a better understanding of these mechanisms.

Consequently, there is a need for the provision of substantial data about bacterial strains that exhibit properties beneficial for man and/or animals. This is now provided by the present invention.

SUMMARY OF THE INVENTION

The above problem has been solved by providing the DNA sequence making up the probiotic strain *Lactobacillus johnsonii* La1.

In one aspect the present invention relates to the use of a nucleotide sequence of the lactic acid bacterium *Lactobacillus johnsonii* La1 genome having the sequence SEQ. ID. NO. 1, parts thereof or sequences homologous thereto for elucidating interactions between bacteria and a host, preferably lactic acid bacteria and a host, more preferably lactobacilli and a host, in particular for determining factors accounting for the probiotic properties of such strains.

In the context of this application the terms genome or genomic sequence shall be understood to mean the sequence of the chromosome of *Lactobacillus johnsonii*. The terms nucleotide sequence, polynucleotide or nucleic acid shall designate a double-stranded DNA, a single-stranded DNA or transcriptional products of the said DNAs of various length including oligo-nucleotides of about 5 to 200, preferably 10 to 100 nucleotides in length.

DETAILED DESCRIPTION OF THE PREFERRED EMBODIMENTS

According to the present invention a homologous nucleotide sequence is understood to mean a nucleotide sequence having a percentual identity with the sequence of SEQ ID. No. 1 (or selected parts thereof) of at least 90%, preferably at least 95%, more preferably 96% and even more preferably at least 98%. The said homologous may comprise, e.g., sequences corresponding to the genomic sequence or to the sequences of fragments thereof belonging to the species *Lactobacillus*, more preferably to the species *Lactobacillus johnsonii*, as well as the sequences corresponding to the genomic sequence or to the sequences of its representative fragments of a bacterium belonging to related species. In the present invention, the terms species and genus are mutually interchangeable.

These homologous sequences may thus correspond to variations linked to mutations within the same species or between species and may correspond in particular to truncations, substitutions, deletions and/or additions of at least one nucleotide. The said homologous sequences may also correspond to variations linked to the degeneracy of the genetic code or to a bias in the genetic code which is specific to the family, to the species or to the variant and which are likely to be present in *Lactobacillus*.

Protein and/or nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (see e.g. Pearson and Lipman, 1988, Proc. Natl. Acad. Sci. USA 85 (8): 2444-2448; Altschul et al., 1990, J. Mol. Biol. 215 (3): 403-410; Thompson et al., 1994, Nucleic Acids Res. 22 (2): 4673-4680; Higgins et al., 1996, Methods Enzymol. 266: 383-402; Altschul et al., 1990, J. Mol. Biol. 215 (3): 403-410; Altschul et al., 1993, Nature Genetics 3: 266-272).

In a particularly preferred embodiment, protein and nucleic acid sequence homologies are evaluated using the Basic Local Alignment Search Tool ("BLAST") which is well known in the art (supra). In particular, four specific BLAST programs have been used to perform the following task:

(1) BLASTP: Compares an amino acid query sequence against a protein sequence database
(2) BLASTN: Compares a nucleotide query sequence against a nucleotide sequence database
(3) BLASTX: Compares a nucleotide query sequence translated in all reading frames against a protein sequence database
(4) TBLASTN: Compares a protein query sequence against a nucleotide sequence database dynamically translated in all reading frames Among these representative fragments, those capable of hybridizing under stringent conditions with a nucleotide sequence disclosed in the present invention are preferred. Hybridization under stringent conditions means that the temperature and ionic strength conditions are chosen such that they allow hybridization to be maintained between two complementary DNA fragments. Such conditions of high stringency may e.g. be achieved by carrying out the hybridisation at a preferred temperature of 65° C. in the presence of SSC buffer, e.g. 1×SSC corresponding to 0.15 M NaCl and 0.05 M Na-citrate. The washing steps may be, for example, the following: 2×SSC, 0.1% SDS at room temperature followed by three washes with 1×SSC, 0.1% SDS; 0.5×SSC, 0.1% SDS; 0.1×SSC, 0.1% SDS at 68 C for 15 minutes.

The nucleotide sequences SEQ. ID. NO. 1 has been obtained by sequencing the genome of *Lactobacillus johnsonii* La1 by the method of directed sequencing after fluorescent automated sequencing of the inserts of clones and assembling of these sequences of nucleotide fragments (inserts) by means of software. To this end, fragments of the genome were created, ligated into suitable vectors for amplification and propagation and the corresponding fragments were sequenced. Overlaps and the final arrangement of the fragments, the nucleotide sequence thereof, were assessed by the aid of appropriate softwares.

Clones for sequencing also included 10'000 bp plus fragments as BAC clones that were used to provide a larger scale framework to the assembly. Due to the presence of several repeated regions a correct assembly proved extremely difficult. These included especially the repeated regions such as IS elements, the ribosomal operons and specifically the genes for two large cell surface proteins that contain between 100 and 200 almost perfect 10 amino acid repeats. In this case the exact sequence of these regions could not be determined due to the inability of current DNA sequencing techniques to cover the region in one run. Internal sequencing primers are excluded as they prime at multiple sites within the gene. Also, the relative orientation of these two genes, their long and very high sequence similarity makes them potential targets for host recombination. While the topology presented here has been confirmed by PCR with appropriate primers, the genome is very probably a product of such a recombination event as implied by the relative positions of the origin and termination of replication. A second problem encountered with the ribosomal operon repeats is that the presence of 6 operons at only 4 loci had been identified, and the exact location of their positions of the extra loci was only difficult to achieve. Finally, two of the IS elements are present in multiple copies, and depending on their replative orientations, they may be targets for host recombination. Such an event has been identified by studying the sequences flanking the IS element, and specifically the chromosomal target sequence that is duplicated on transposition, and hence each IS element should be flanked by identical direct repeats. We have identified two IS elements where the direct repeats have been switched due to host recombination within the IS elements. This produces an approximately 600'000 bp inversion that has been confirmed by PCR with specific primers. This IS element specific recombination may be a dynamic event that is taking place within a growing culture, leading to a major species plus a small presence of the recombined genome (seen as a faint PCR band). Finally we have the case of the prophage L771 (approximately 40'000 bp) that is constantly being excised by a site-specific recombinase. We have developed a quantitative PCR technique to detect the presence and measure the relative abundance of each variant. No pure cultures have been prepared to date.

Particularly preferred fragments of the nucleic acid sequence as identified by SEQ. ID. No. 1 are from 1-54596, from 56070-77430, from 81302-308537, from 309588-342757, from 378458-389217, from 389779-404510, from 405561-501116, from 503873-558194, from 563262-696518, from 697569-721736, from 722787-756845, from 761682-860446, from 860723-865550, from 867260-867490, from 868541-1448288, from 1463851-1526077, from 1527278-1552024, from 1563147-1809115, from 1810166-1858190, from 1863258-1872871, from 1877939-1930430, from 1932063-1983043, based on the numbering of SEQ ID. No. 1, each.

The present invention may also be utilized for producing polypeptides by using the knowledge of open reading frames (ORFs) as derived from SEQ. ID. NO. 1 and expressing the polypeptide desired according to well known techniques. In this respect, a nucleic acid corresponding to an open reading frame may be selected and inserted into an expression vector. The vector may then be introduced into a host, that enables transcription and translation of the open reading frame into the polypeptide under suitable conditions.

Nucleic acid molecules derived from the genomic sequence as identified by SEQ. ID. NO. 1 may easily be obtained, by e.g. specific amplification of the corresponding sequence using the polymerase chain reaction. Due to the sequence information provided herein the skilled person may design and synthesize any suitable primer nucleotide and amplify a fragment of interest using the polymerase chain reaction. Therefore, the present invention also comprises nucleotide sequences selected from sequence SEQ. ID. NO. 1 which can be used as a primer for the amplification of nucleic acid sequences. Other techniques for amplifying the target nucleic acid may of course also be used, such as e.g. the TAS (Transcription-based Amplification System) technique, the 3SR (Self-Sustained Sequence Replication) technique, the NASBA (Nucleic Acid Sequence Based Amplification) technique, the SDA (Strand Displacement Amplification) technique or the TMA (Transcription Mediated Amplification) technique etc.

The (poly)nucleotides may be used as probes and techniques for amplifying or modifying a nucleic acid serving as a probe, such as e.g. the LCR (Ligase Chain Reaction) technique, the RCR (Repair Chain Reaction) technique, the CPR (Cycling Probe Reaction) technique or the Q-beta-replicase amplification technique may well be applied.

The present invention, therefore, envisages both hybridization (detection) probes and primers for detecting a nucleotide sequence (target nucleotide) of the present invention. In the case of the target being a RNA molecule, e.g. a mRNA, said mRNA may be directly detected or transformed to a cDNA prior to detection.

Alternatively, in order to obtain fragments of the nucleic acid represented by SEQ. ID. NO. 1 the *Lactobacillus johnsonii* genomic DNA may be subjected to digestion with selected restriction enzymes, with the fragments being separated by e.g. electrophoresis or another suitable separation technique. Such techniques are well known in the art and are inter alia disclosed in Sambrook et al. A Laboratory Manual, Cold Spring Harbor, 1992. Such fragments may easily be obtained by isolating the genomic DNA of *Lactobacillus johnsonii* La1 and performing the necessary steps.

In an alternative form the nucleic acids may also be obtained by chemical synthesis when they are not too large in size according to methods well known to a person skilled in the art.

Modified nucleotide sequences shall be understood to mean any nucleotide sequence obtained by mutagenesis according to techniques well known to a skilled person and exhibiting modifications in relation to the normal sequences, for example mutations in the regulatory and/or promoter sequences for the expression of a polypeptide, in particular leading to a modification of the level of expression of the said polypeptide or to a modulation of the replicative cycle. Modified nucleotide sequence will also be understood to mean any nucleotide sequence encoding a modified polypeptide as defined herein.

During the study of the *Lactobacillus johnsonii* genome the following open reading frames could be determined with an annotation of the function of the resulting polypeptide being possible on the basis of homology to known proteins.

TABLE I

| Gene | Start | Stop | Complement* | % ID | Function |
|---|---|---|---|---|---|
| LJ_0008 (78 aa*) | 9756 | 9992 | | 84.8 | Ribosomal protein S18 |
| LJ_0043 (384 aa) | 52848 | 54002 | complement | 76.4 | INOSINE-5'-MONOPHOSPHATE DEHYDROGENASE (EC 1.1.1.205) |
| LJ_0045 (337 aa) | 54728 | 55741 | complement | 96.7 | D-lactate dehydrogenase (EC 1.1.1.28) |
| LJ_0054 (304 aa) | 75671 | 76585 | | 93 | Prolinase prolyl aminopeptidase (EC 3.4.11.5) |
| LJ_0056 (316 aa) | 77465 | 78415 | complement | 99 | Conjugated bile salt hydrolase (EC 3.5.1.24) |
| LJ_0057 (451 aa) | 78431 | 79786 | complement | 88 | Putative bile salt transporter |
| LJ_0058 (452 aa) | 79810 | 81168 | complement | 81.4 | Putative bile salt transporter |
| LJ_0065 (235 aa) | 87816 | 88523 | | 74.6 | Response regulator |
| LJ_0124 (149 aa) | 146032 | 146481 | complement | 80.4 | Nucleoside deoxyribosyltransferase-II (EC 2.4.2.6) |
| LJ_0178 (436 aa) | 211269 | 212579 | complement | 71.1 | Aminopeptidase G (EC 3.4.22.-) |
| LJ_0182 (482 aa) | 214451 | 215899 | complement | 98.7 | 6-PHOSPHO-BETA-GLUCOSIDASE (EC 3.2.1.86) |
| LJ_0215 (367 aa) | 248929 | 250032 | | 70.2 | Multiple sugar-binding transport ATP-binding protein msmK. (EC 2.7.1.69) |
| LJ_0229 (517 aa) | 264155 | 265708 | | 75.2 | GMP synthase [glutamine-hydrolyzing] (EC 6.3.5.2) |
| LJ_0258 (471 aa) | 287474 | 288889 | complement | 85.9 | Dipeptidase A (EC 3.4.*.*) |
| LJ_0260 (653 aa) | 290018 | 291979 | | 75 | Raffinose carrier protein (RAFFINOSE PERMEASE) |
| LJ_0262 (480 aa) | 294170 | 295612 | | 71.6 | sucrose phosphorylase (EC 2.4.1.7) |
| LJ_0274 (323 aa) | 307454 | 308425 | complement | 84.4 | L-lactate dehydrogenase (EC 1.1.1.27) |
| LJ_0295 (249 aa) | 332973 | 333722 | | 79.7 | ORF 169a (prophage protein) |
| LJ_0307 (284 aa) | 343364 | 344218 | | 100 | terminase small subunit (prophage protein) |
| LJ_0308 (424 aa) | 344205 | 345479 | | 100 | orf345; terminase large subunit (prophage protein) |
| LJ_0309 (499 aa) | 345495 | 346994 | | 99.7 | orf500; putative portal protein (prophage protein) |
| LJ_0311 (360 aa) | 347218 | 348300 | | 100 | orf360; putative minor head protein (prophage protein) |
| LJ_0312 (214 aa) | 348455 | 349099 | | 100 | orf214; scaffold protein (prophage protein) |
| LJ_0313 (121 aa) | 349112 | 349477 | | 100 | Orf121 (prophage protein) |
| LJ_0314 (349 aa) | 349498 | 350547 | | 100 | orf349; major head protein (prophage protein) |
| LJ_0315 (105 aa) | 350557 | 350874 | | 99 | Orf105 (prophage protein) |
| LJ_0316 (117 aa) | 350871 | 351224 | | 100 | Orf117 (prophage protein) |
| LJ_0317 (182 aa) | 351217 | 351765 | | 99 | Orf106 (prophage protein) |
| LJ_0318 (122 aa) | 351766 | 352134 | | 100 | Orf122 (prophage protein) |
| LJ_0319 (159 aa) | 352137 | 352616 | | 100 | orf159; putative major tail protein (prophage protein) |
| LJ_0320 (136 aa) | 352694 | 353104 | | 93.3 | Orf136 (prophage protein) |
| LJ_0321 (97 aa) | 353197 | 353490 | | 100 | Orf109 (prophage protein) |
| LJ_0322 (2021 aa) | 353490 | 359555 | | 92.6 | orf1434; putative minor tail protein (prophage protein) |
| LJ_0323 (118 aa) | 359573 | 359929 | | 99 | Orf109a (prophage protein) |
| LJ_0324 (1624 aa) | 359943 | 364817 | | 100 | Orf977 (prophage protein) |
| LJ_0325 (86 aa) | 364949 | 365209 | | 100 | Orf86 (prophage protein) |
| LJ_0326 (135 aa) | 365209 | 365616 | | 100 | Orf135 (prophage protein) |
| LJ_0327 (85 aa) | 365626 | 365883 | | 88.2 | Orf85 (prophage protein) |
| LJ_0328 (115 aa) | 365876 | 366223 | | 100 | orf115; putative holin (prophage protein) |
| LJ_0329 (310 aa) | 366216 | 367148 | | 99.6 | orf376; lysin (prophage protein) |
| LJ_0332 (1209 aa) | 370820 | 374449 | | 70.9 | rpoB; RNA polymerase (beta subunit) (EC 2.7.7.6) |
| LJ_0333 (1224 aa) | 374470 | 378144 | | 70 | rpoC; RNA polymerase (beta subunit) (EC 2.7.7.6) |
| LJ_0335 (135 aa) | 379054 | 379461 | | 85.8 | RS12; ribosomal protein S12 |
| LJ_0336 (156 aa) | 379485 | 379955 | | 76.7 | RS7; 30S ribosomal protein S7 |

TABLE I-continued

| Gene | Start | Stop | Complement* | % ID | Function |
|---|---|---|---|---|---|
| LJ_0337 (698 aa) | 379985 | 382081 | | 70.7 | translation elongation factor G, EF-G |
| LJ_0339 (209 aa) | 382686 | 383315 | | 73.4 | rplC; 50S ribosomal protein L3 |
| LJ_0342 (278 aa) | 384263 | 385099 | | 75.1 | rplB; 50S ribosomal protein L2 |
| LJ_0343 (95 aa) | 385121 | 385408 | | 81.1 | rpsS; 30S ribosomal protein S19 |
| LJ_0344 (117 aa) | 385429 | 385782 | | 75.4 | rplV; ribosomal protein L22 |
| LJ_0345 (222 aa) | 385800 | 386468 | | 70 | 30S ribosomal protein S3 |
| LJ_0346 (145 aa) | 386468 | 386905 | | 84.8 | ribosomal protein L16 |
| LJ_0347 (88 aa) | 387118 | 387384 | | 72 | 30S RIBOSOMAL PROTEIN S17 |
| LJ_0348 (122 aa) | 387415 | 387783 | | 72.9 | rplN; ribosomal protein L14 |
| LJ_0350 (180 aa) | 388058 | 388600 | | 79.7 | RL5; ribosomal protein L5 (BL6) |
| LJ_0351 (132 aa) | 388825 | 389223 | | 70.4 | rpsH; 30S Ribosomal protein S8 |
| LJ_0352 (176 aa) | 389248 | 389778 | | 98.2 | lecLA2-20; lectin-like protein LA2-20 |
| LJ_0353 (119 aa) | 389806 | 390165 | | 72.2 | rplR; 50S ribosomal protein L18 |
| LJ_0358 (73 aa) | 393402 | 393623 | | 84.5 | Translation initiation factor IF-1 |
| LJ_0359 (115 aa) | 393788 | 394135 | | 73.6 | rpsM; ribosomal protein S13 |
| LJ_0360 (129 aa) | 394160 | 394549 | | 73 | rpsK; 30S Ribosomal protein S11 |
| LJ_0362 (127 aa) | 395560 | 395943 | | 73.2 | rplQ; 50S Ribosomal protein L17 |
| LJ_0368 (131 aa) | 399970 | 400365 | | 70 | 30S RIBOSOMAL PROTEIN S9 |
| LJ_0395 (449 aa) | 441168 | 442517 | complement | 81.5 | Aminopeptidase C (EC 3.4.22.40) |
| LJ_0399 (499 aa) | 445878 | 447377 | | 73.5 | Glutamyl-tRNA synthetase (EC 6.1.1.17) |
| LJ_0410 | 458506 | 458931 | | 77 | 50S ribosomal protein L11 |
| LJ_0441 (330 aa) | 483735 | 484727 | complement | 70.6 | GMP reductase (EC 1.6.6.8) |
| LJ_0460 (94 aa) | 501772 | 502056 | | 99 | GroES chaperone |
| LJ_0461 (543 aa) | 502087 | 503718 | | 99 | GroEL chaperone |
| LJ_0490 (368 aa) | 543751 | 544857 | complement | 75.2 | pepQ; Xaa-Pro dipeptidase (EC 3.4.13.9) |
| LJ_0493 (465 aa) | 548984 | 550341 | complement | 71.6 | pepV; Xaa-His dipeptidase (EC 3.4.13.3) |
| LJ_0505 (309 aa) | 565393 | 566322 | | 73.1 | Mannose-specific phosphotransferase system comp. IID (EC 2.7.1.69) |
| LJ_0521 (536 aa) | 583645 | 585255 | | 79 | Putative ABC transporter |
| LJ_0563 (228 aa) | 623532 | 624218 | | 83.7 | putative response regulator |
| LJ_0631 (158 aa) | 705767 | 706243 | complement | 74 | Autoinducer protein luxS |
| LJ_0677 (402 aa) | 762315 | 763523 | | 70 | metK; S-adenosylmethionine synthetase (EC 2.5.1.6) |
| LJ_0764 (435 aa) | 859739 | 861046 | | 100 | putative sensor histidine kinase |
| LJ_0767 (719 aa) | 863354 | 865513 | | 77.9 | Sequence from patent |
| LJ_0768 (197 aa) | 865524 | 866117 | | 91.4 | Lacticin F transporter accesory protein |
| LJ_0769 (75 aa) | 866244 | 866471 | | 98.6 | Bacteriocin lactacin F, subunit lafA precursor |
| LJ_770 (62 aa) | 866485 | 866671 | | 100 | Bacteriocin lacticin F, subunit lafX precursor |
| LJ_0771 (124 aa) | 866757 | 867131 | | 90.3 | Bacteriocin lacticin F immunity protein, lafI |
| LJ_0775 (719 na) | 869095 | 871254 | | 77.9 | Sequence from patent |
| LJ_0776 (197 aa) | 871265 | 871858 | | 77.1 | Hypothetical protein |
| LJ_0817 (88 aa) | 910392 | 910658 | | 79.5 | Phosphocarrier protein HPr |
| LJ_0827 (591 aa) | 918499 | 920274 | | 71 | Sequence from patent |
| LJ_0840 (360 aa) | 932899 | 933981 | | 72 | recA; Recombinase A |
| LJ_0846 (181 aa) | 939718 | 940263 | | 80.1 | Hypothetical protein |
| LJ_0847 (799 aa) | 940421 | 942820 | | 81.9 | preprotein translocase SecA subunit |
| LJ_0848 (332 aa) | 943020 | 944018 | | 72.5 | peptide chain release factor 2 |
| LJ_0853 (311 aa) | 947228 | 948163 | | 71.8 | trxB; THIOREDOXIN REDUCTASE (EC 1.6.4.5) |
| LJ_0855 (317 aa) | 949277 | 950230 | complement | 71 | lacM; Beta-galactosidase small subunit (EC 3.2.1.23) |
| LJ_0856 (626 na) | 950211 | 952091 | complement | 75.2 | lacL; Beta-galactosidase large subunit (EC 3.2.1.23) |
| LJ_0860 (389 aa) | 957611 | 958780 | | 76.8 | galK; Galactokinase (EC 2.7.1.6) (Galactose kinase) |
| LJ_0861 (495 aa) | 958799 | 960286 | | 74.7 | galT; Galactose-1-phosphate uridylyltransferase (EC 2.7.7.10) |
| LJ_0864 (671 aa) | 963226 | 965241 | | 76.9 | uvrB; EXCINUCLEASE ABC SUBUNIT B |
| LJ_0870 (195 aa) | 971745 | 972332 | complement | 70 | clpP, ATP-dependent Clp protease proteolytic subunit (EC 3.4.21.92) |
| LJ_0873 (338 aa) | 975442 | 976458 | | 87.8 | gapdh; Glyceraldehyde 3-phosphate dehydrogenase (EC 1.2.1.12) |
| LJ_0874 (403 aa) | 976565 | 977776 | | 84.3 | pgk; Phosphoglycerate kinase (EC 2.7.2.3) |
| LJ_0875 (251 aa) | 977795 | 978550 | | 84.8 | tim; Triosephosphate isomerase (EC 5.3.1.1) |
| LJ_0876 | 978600 | 979898 | | 71 | Enolase (EC 4.2.1.11) (2-phosphoglycerate dehydratase) |
| LJ_0925 (447 aa) | 1023089 | 1024432 | | 72.5 | Glucose-6-phosphate isomerase (EC 5.3.1.9) |
| LJ_0934 (203 aa) | 1032968 | 1033579 | | 73.7 | uracil phosphoribosyltransferase (EC 2.4.2.9) |
| LJ_0936 (70 aa) | 1034425 | 1034637 | | 73.9 | atpE; F1F0-ATPase subunit c (EC 3.6.1.34) |
| LJ_0937 (166 aa) | 1034690 | 1035190 | | 70 | atpF, F1F0-ATPase subunit b (EC 3.6.1.34) |
| LJ_0939 (503 aa) | 1035750 | 1037261 | | 84.8 | atpA; F1F0-ATPase subunit alpha (EC 3.6.1.34) |
| LJ_0941 (480 aa) | 1038258 | 1039700 | | 84.7 | atpD; F1F0-ATPase subunit beta (EC 3.6.1.34) |
| LJ_0954 (384 aa) | 1049212 | 1050366 | | 70.8 | nifS; pyridoxal-phosphate dependent aminotransferase (EC 4.4.1.-) |
| LJ_0976 (458 aa) | 1074934 | 1076310 | | 73 | CELL DIVISION PROTEIN FTSZ |
| LJ_0996 (618 aa) | 1093985 | 1095841 | | 70 | elongation factor Tu family protein |
| LJ_1007 (89 aa) | 1103999 | 1104268 | | 71.9 | rpsO; 30S ribosomal protein S15 |
| LJ_1010 (396 aa) | 1107239 | 1108429 | | 74 | EF-Tu; Elongation factor Tu |
| LJ_1033 (372 aa) | 1129276 | 1130394 | | 85.8 | Sequence from patent |
| LJ_1079 (319 aa) | 1181384 | 1182343 | | 76.1 | K6PF; 6-phosphofructokinase (EC 2.7.1.11) |
| LJ_1080 (589 aa) | 1182378 | 1184147 | | 83 | pyk; Pyruvate kinase (EC 2.7.1.40) |
| LJ_1092 (91 aa) | 1193710 | 1193985 | | 77.5 | hu; DNA-binding protein II |
| LJ_1111 (174 aa) | 1215382 | 1215906 | | 83.9 | hslU; heat shock induced protein HtpI |
| LJ_1112 (464 aa) | 1215917 | 1217311 | | 76.1 | HSLU; ATP-dependent hsl protease ATP-binding subunit hslU. |
| LJ_1138 264 aa) | 1255582 | 1256376 | | 70 | ABC transporter ATP-binding protein |
| LJ_1170 (661 aa) | 1287817 | 1289802 | | 71 | topoisomerase IV B subunit (EC 5.99.1.*) |

TABLE I-continued

| Gene | Start | Stop | Complement* | % ID | Function |
|---|---|---|---|---|---|
| LJ_1200 (432 aa) | 1324275 | 1325573 | complement | 83.5 | asnA1; Asparaginyl-tRNA synthetase (EC 6.1.1.22) |
| LJ_1207 (357 aa) | 1338065 | 1339138 | | 70.1 | pmk; phosphomevalonate kinase (EC 2.7.1.36) |
| LJ_1298 (75 aa) | 1425244 | 1425471 | | 71.8 | tpnA; transposase, fragment only |
| LJ_1303 (415 aa) | 1428575 | 1429822 | complement | 85.4 | pepT, PEPTIDASE T (EC 3.4.11.-) (aminotripeptidase) (tripeptidase) |
| LJ_1304 (265 aa) | 1429834 | 1430631 | complement | 81.1 | Hypothetical protein |
| LJ_1317 (372 aa) | 1441016 | 1442134 | complement | 81.4 | rpoD; RNA polymerase sigma factor rpoD (Sigma-42) |
| LJ_1320 (305 aa) | 1446050 | 1446967 | complement | 70.4 | glyQ; Glycyl-tRNA synthetase alpha chain (EC 6.1.1.14) |
| LJ_1389 (142 aa) | 1457128 | 1457556 | complement | 71.7 | Peptide methionine sulfoxide reductase (EC 1.8.4.6) |
| LJ_1356 (326 aa) | 1484903 | 1485883 | complement | 99 | conjugated bile salt hydrolase bile (EC 3.5.1.24) |
| LJ_1384 (470 aa) | 1510322 | 1511734 | complement | 100 | orf338; putative portal protein (prophage protein) |
| LJ_1385 (422 aa) | 1511746 | 1513014 | complement | 100 | orf42; terminase large subunit (prophage protein) |
| LJ_1386 (151 aa) | 1513007 | 1513462 | complement | 100 | orf155; terminase small subunit (prophage protein) |
| LJ_1387 (218 aa) | 1513519 | 1514175 | complement | 100 | Orf221 (prophage protein) |
| LJ_1388 (174 aa) | 1514357 | 1514881 | complement | 90.5 | Orf174 (prophage protein) |
| LJ_1389 (146 aa) | 1515925 | 1516365 | complement | 100 | Orf154 (prophage protein) |
| LJ_1390 (73 aa) | 1516454 | 1516675 | complement | 100 | Orf85 (prophage protein) |
| LJ_1391 (184 aa) | 1516695 | 1517249 | complement | 93.4 | Orf197 (prophage protein) |
| LJ_1392 (132 aa) | 1517251 | 1517649 | complement | 82.6 | Orf79 (prophage protein) |
| LJ_1393 (71 aa) | 1517650 | 1517865 | complement | 96.5 | Orf78a (prophage protein) |
| LJ_1394 (296 aa) | 1518025 | 1518915 | complement | 98.1 | Orf212 (prophage protein) |
| LJ_1395 (261 aa) | 1518928 | 1519713 | complement | 93.9 | Orf223 (prophage protein) |
| LJ_1396 (297 aa) | 1519715 | 1520608 | complement | 100 | Orf309 (prophage protein) |
| LJ_1397 (71 aa) | 1521285 | 1521500 | complement | 100 | Orf73 (prophage protein) |
| LJ_1415 (318 aa) | 1534064 | 1535020 | complement | 71.4 | thyA; thymidylate synthase (EC 2.1.1.45) |
| LJ_1423 (624 aa) | 1545410 | 1547284 | complement | 85.3 | dnaK; heat shock protein DnaK |
| LJ_1431 (880 aa) | 1553796 | 1556438 | complement | 70.3 | IF2; Translation initiation factor IF-2. |
| LJ_1442 (241 aa) | 1568288 | 1569013 | complement | 70.5 | pyrH; UMP-kinase (EC 2.7.4.-) |
| LJ_1444 (261 aa) | 1570186 | 1570971 | complement | 75.6 | RS2; 30S ribosomal protein S2. |
| LJ_1446 (125 aa) | 1581060 | 1581437 | complement | 76.1 | RL19; 50S ribosomal protein L19. |
| LJ_1447 (84 aa) | 1605746 | 1606000 | | 80 | RL28; 50S ribosomal protein L28. |
| LJ_1429 (794 aa) | 1656725 | 1659109 | | 71.5 | pepX; Xaa-Pro dipeptidyl-peptidase (EC 3.4.14.11) |
| LJ_1537 (301 aa) | 1666162 | 1667067 | complement | 71.2 | galU; UDP-glucose pyrophosphorylase, (EC 2.7.7.9) |
| LJ_1558 (445 aa) | 1686863 | 1688200 | complement | 72.8 | Glutamine synthetase (EC 6.3.1.2) (Glutamate--ammonia ligase) |
| LJ_1584 (118 aa) | 1713330 | 1713686 | complement | 70.7 | RL20; 50S ribosomal protein L20 |
| LJ_1681 (128 aa) | 1826901 | 1827287 | | 72.6 | tagD; Glycerol-3-phosphate cytidylyltransferase (EC 2.7.7.39) |
| LJ_1741 (215 aa) | 1902945 | 1903592 | complement | 72.5 | Pyrrolidone-carboxylate peptidase (EC 3.4.19.3) |
| LJ_1767 (215 aa) | 1930610 | 1931257 | | 100 | deoxyadenosine kinase (EC 2.7.1.76) |
| LJ_1768 (224 aa) | 1931279 | 1931953 | | 99.1 | deoxyguanosine kinase (EC 2.7.1.113) |

*complement = on the reverse strand
*aa = amino acids

The ORFs corresponding to various polypeptides are shown in table 1, supra, and are represented by their position in the genomic sequence as identified by SEQ. ID. NO. 1.

The open reading frames have been identified via homology analyses as well as via analyses of potential ORF start sites. It is to be understood that each identified ORF comprises a nucleotide sequence that spans the contiguous nucleotide sequence from the codon immediately 3' to the stop codon of the preceding ORF and through the 5' codon to the next stop codon of SEQ. ID. NO. 1 in frame to the ORF nucleotide sequence.

Table 1 also depicts the results of homology searches that compared the sequences of the polypeptides encoded by each of the ORFs to sequences present in databases.

The sequence information disclosed in the present application may be utilized for selecting a polynucleotide of interest, i.e. a nucleic acid containing an open reading frame encoding a known or an unknown, putative polypeptide and transforming micro-organisms with the selected polynucleotide. As transformation vehicles the well known plasmids, phage vectors (transfection) or F-vectors (conjugation) may be utilized. The nucleic acid introduced into the micro-organism selected may be expressed and its biological function may be either utilized as such, if known, or elucidated, in case a so far unknown polypeptide is expressed. The micro-organism selected may be a *Lactobacillus* itself or other well known micro-organisms, such as bacteria, e.g. *E. coli, Streptococci* or yeast, insect cells or even animal and plant cells.

It will be understood that the polypeptides may be expressed as such or as a fusion polypeptide. The skilled person is well aquatinted with techniques performing such a ligation and expressing the corresponding fusion-polypeptide in an appropriate cell.

In view of the present invention also new recombinant vectors for the cloning and/or the expression of a nucleotide sequence according to the present invention may be devised. The vectors comprise elements necessary to enable expression and/or secretion of the nucleotide sequences in a given host cell, such as a promoter, signals for initiation and for termination of translation, as well as appropriate regions for regulation of transcription. For example, expression of a protein or peptide may be controlled by any promoter/enhancer element known in the art. Exemplary promotors are the CMV promoter, the SV40 early promoter region, the promoter contained in the 3' long terminal repeat of the rous sarcoma virus, the herpes thymidine kinase promoter, the regulatory sequences of the metallothionein gene, or, for prokaryotic expression systems, the β-lactamase promoter, the tac promoter or the T7 promoter.

The vector should be capable of being stably maintained in the host cell and may optionally possess particular signals specifying the secretion of the translated protein. These different elements are chosen according to the host cell utilized. To this effect the nucleotide sequences according to the invention may be inserted into autonomously-replicating vectors within the chosen host, or integrative vectors in the chosen host, such as e.g. yeast artificial chromosomes, plasmids or viral vectors.

Any of the standard methods known to those skilled in the art for inserting DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

The vector may be used for transcription and/or translation of a nucleic acid comprised in SEQ. ID. NO. 1, to produce RNA or antisense RNA, respectively. Such a vector can remain episomal or become chromosomally integrated, as long as it can be transcribed to produce the desired transcript.

The antisense nucleic acids of the invention comprise a sequence complementary to at least a portion of a RNA transcript of a polynucleotide sequence in SEQ. ID. NO. 1, designating a sequence having sufficient complementarity to be able to hybridize with the RNA, forming a stable duplex. In the case of double-stranded antisense nucleic acid sequence, a single strand of the duplex DNA may thus be tested, or triplex formation may be assayed.

In knowledge of the present invention also host cells may be obtained transformed with a nucleic acid or a vector according described herein. These cells may be attained by introducing into an appropriate cell a nucleotide sequence or a vector as defined above, and then culturing the said cell under conditions allowing the replication and/or the expression of the transformed/transfected nucleotide sequence.

The host cell may be chosen from eukaryotic or prokaryotic system, such as for example bacterial cells, yeast cells, animal cells as well as plant cells. In the context of this invention a cell shall be understood to comprise higher biological systems. Such as animals, whole plants or parts thereof.

Furthermore, a host cell strain may be chosen which modulates the expression of the inserted sequences, or modifies and processes the gene product in the specific fashion desired.

A preferred host cell for the expression of the proteins of the invention consists of prokaryotic cells, such as gram negative or gram positive bacteria. A further preferred host cell according to the invention is a bacterium belonging to the *Lactobacillus* family, more preferably belonging to the species *Lactobacillus johnsonii* or chosen from a microorganism associated with the species *Lactobacillus*.

The transformed/transfected cells according to the invention may advantageously serve as a model and may be used in methods for studying, identifying and/or selecting compounds capable of being responsible for any of the beneficial effects brought about by the present *Lactobacillus* strain.

The invention further enables the synthesis of polypeptides encoded by the *Lactobacillus johnsonii* ORFs, in particular those listed in table 1. In the present description, the terms polypeptide, peptide and protein are used interchangeably. Furthermore the present invention also enables to carry out method for preparing such polypeptides by recombinant means comprising the steps of (a) culturing a host cell according to the present invention under conditions suitable to produce the polypeptide encoded by the polynucleotide; and (b) recovering the polypeptide from the culture.

It will be appreciated that the above polypeptides may also be obtained using combinatory chemistry, wherein the polypeptide is modified at some locations before testing them in model systems, so as to select the compounds which are the most active or which exhibit the desired properties.

In this context, chemical synthesis has the advantage of being able to use non-natural amino acids or non-peptide bonds. Accordingly, in order to e.g. extend the life of the polypeptides according to the invention, it may be advantageous to use such non-natural amino acids, for example in the D form, or alternatively amino acid analogues, preferably sulphur-containing forms.

Finally, the structure of the polypeptides according to the invention, its homologous or modified forms, as well as the corresponding fragments may be integrated into chemical structures of the polypeptide type and the like. Accordingly, in order to preserve the polypeptide in an in vivo environment it will be preferred to provide at the N- and C-terminal ends compounds which convey a resistance to degradation to proteases.

It will also be appreciated that the different polypeptides according to the present invention and produced by the above method may represent antigens to the immune system of a host animal, so that antibodies may be produced directed against said polypeptides. These antibodies may be used for the detection of a polypeptide of interest in a mixture or generically of a strain of *Lactobacillus* in a sample. In addition they may be used as research tools by e.g. producing antibodies against cellular surface epitopes and determining the effect of blocking certain polypeptides on the bacterial cell wall.

According to another aspect the present invention also provides a method for the detection and/or identification of *Lactobacilli*, preferably *Lactobacillus johnsonii* in a biological sample. This method may comprise several techniques known in the art, such as PCR or simply hybridization with a suitable probe. Alternatively, an antibody raised against a cell wall epitope of *Lactobacillus*, preferably *Lactobacillus johnsonii* may be used for said purpose. It will be appreciated that the above method may also be reversed and the presence of antibodies against *Lactobacillus* may be determined by contacting the sample to be tested with a polypeptide of *Lactobacillus* under conditions to allow formation of immune complexes.

The polypeptides and antibodies obtainable in knowledge of the present invention and the nucleotide sequences described herein may be used in in vitro and/or in vivo methods for the detection and/or the identification of bacteria belonging to the species *Lactobacillus* in a biological sample (biological tissue or fluid) which is likely to contain them. These methods, depending on the specificity of the polypeptides, of the antibodies and of the nucleotide sequences described herein, which will be used, may detect and/or identify the bacterial variants belonging to the species *Lactobacillus* as well as associated microorganisms capable of being detected by the polypeptides, the antibodies and the nucleotide sequences according to the invention which will be chosen. It may, for example, be advantageous to choose a polypeptide, an antibody or a nucleotide sequence according to the invention, which is capable of detecting any bacterium of the *Lactobacillus* family by choosing a polypeptide, an antibody and/or a nucleotide sequence according to the invention which is specific to the family.

The sequences referred to herein SEQ ID. NO. 1 is listed in the attached sequence listings which is to be considered as part of the specification.

The invention also comprises the nucleotide sequences or polypeptides according to the invention covalently or non-covalently immobilized on a solid support. In the first case such a support may serve to capture, through specific hybridization, the target nucleic acid obtained from a biological sample to be tested. If necessary, the solid support is separated from the sample and the hybridization complex formed between the capture probe and the target nucleic acid is then detected by means of a second probe, called detection probe, labeled with an easily detectable element.

Such support may take the form of so-called DNA array or DNA chips, a multitude of molecular probes precisely organized or arrayed on a solid support, which will allow sequencing genes, studies of mutations contained therein and the expression of genes, and which are currently of interest given their very small size and their high capacity in terms of number of analyses.

The function of these arrays/chips is based on molecular probes, mainly oligonucleotides which are attached to a carrier having a size of generally a few square centimetres or more as desired. For an analysis the carrier (DNA array/chip) is coated with probes that are arranged at a predetermined location of the carrier. A sample containing fragments of a target nucleic acid to be analyzed, for example DNA or RNA or cDNA, that has been labeled beforehand, is subsequently contacted with the DNA array/chip leading to the formation, through hybridization, of a duplex. After a washing step, analysis of the surface of the chip allows the effective hybridization to be located by means of the signals emitted by the labels tagging the target. A hybridization fingerprint results from this analysis which, by appropriate computer processing, allows to retrieve information such as the expression of genes, the presence of specific fragments in the sample, the determination of sequences and the presence of mutations.

The hybridization between the probes of the invention, deposited or synthesized in situ on the DNA chips, and the sample to be analyzed, may, e.g. be determined by means of fluorescence, radioactivity or by electronic detection.

The nucleotide sequences according to the invention may be used in DNA arrays/chips to carry out analyses of the expression of the *Lactobacillus* genes. This analysis is based on DNA arrays/chips on which probes, chosen for their specificity to characterize a given gene, are present. The target sequences to be analyzed are labeled before being hybridized onto the chip. After washing the labeled compounds are detected and quantified, with the hybridization being carried out at least in duplicate. Comparative analyses of the signal intensities obtained with respect to the same probe for different samples and/or for different probes with the same sample, determine a differential transcription of RNA derived from the sample.

The DNA arrays/chips according to the present invention may also contain nucleotide probes specific for other microorganisms, which will enable a serial testing allowing rapid identification of the presence of a microorganism in a sample.

The principle of the DNA chip, as detailed above may also be used to produce protein chips on which the support has been coated with a polypeptide or an antibody according to the invention, or arrays thereof, in place of the DNA. These protein chips make it possible to analyze the biomolecular interactions (BIA) induced by the affinity capture of target analytes onto a support coated e.g. with proteins, by surface plasma resonance (SPR). The polypeptides or antibodies according to the invention, capable of specifically binding antibodies or polypeptides derived from the sample to be analyzed, may thus be used in protein chips for the detection and/or the identification of proteins in samples.

The present invention also relates to a computer readable medium having recorded thereon one or more nucleotide and/or a polypeptide sequences according to the invention. This medium may also comprise additional information extracted from the present invention, such as e.g. analogies with already known sequences and/or information relating to the nucleotide and/or polypeptide sequences of other microorganisms so as to facilitate the comparative analysis and the exploitation of the results obtained. Preferred media are e.g. magnetic, optical, electrical and hybrid media such as, for example, floppy disks, CD-ROMs or recording cassettes.

The invention also relates to kits or sets for the detection and/or the identification of bacteria belonging to the species *Lactobacillus johnsonii* or to associated microorganisms, which comprises, a polypeptide according to the invention, where appropriate, the reagents for constituting the medium appropriate for the immunological or specific reaction, the reagents allowing the detection of the antigen-antibody complexes produced by the immunological reaction between the polypeptide (s) of the invention and the antibodies which may be present in the biological sample, it being possible for these reagents also to carry a label, or to be capable of being recognized in turn by a labeled reagent, more particularly in the case where the polypeptide according to the invention is not labeled, a reference biological sample (negative control) free of antibodies recognized by a polypeptide according to the invention, a reference biological sample (positive control) containing a predetermined quantity of antibodies recognized by a polypeptide according to the invention.

The invention also relates to a kit or set for the detection and/or the identification of bacteria belonging to the species *Lactobacillus johnsonii* or to an associated microorganism, or for the detection and/or the identification of a microorganism, wherein the kit comprises a protein chip according to the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07875421B2). An electronic copy of the "Sequence Listing" will also be available from the USPTO upon request and payment of the fee set forth in 37 CFR 1.19(b)(3).

What is claimed is:

1. A method for elucidating a biological function of a protein involved in an interaction between a host and a bacteria, said method comprising:

introducing a nucleotide sequence comprising an entire open reading frame that codes for the protein into the bacteria;

expressing the protein in the bacteria;

contacting the host with the bacteria; and determining the interaction between the host and the bacteria, wherein the interaction between the host and the bacteria elucidates the function of the protein and wherein the nucleotide sequence that comprises an entire open reading frame coding for the protein is SEQ ID NO: 1 or a fragment thereof.

2. The method according to claim 1, wherein the protein functions as a probiotic, anti-pathogenic or anti-viral.

3. The method according to claim 1, wherein the protein functions as a probiotic for stimulating the immune system.

4. The method according to claim 1, wherein the fragment of SEQ ID. No. 1 is selected from the group consisting of: nucleotides 1-54596, 56070-77430; 81302-308537, 309588-342757, 378458-389217, 389779-404510, 405561-501116, 503873-558194, 563262-696518, 697569-721736, 722787-756845, 761682-860446, 860723-865550, 867260-867490, 868541-1448288, 1463851-1526077, 1527278-1552024, 1563147-1809115, 1810166-1858190, 1863258-1872871, 1877939-1930430, and 1932063-1983043, based on the numbering of SEQ ID. No. 1.

* * * * *